(12) United States Patent
Laine et al.

(10) Patent No.: US 9,699,977 B2
(45) Date of Patent: *Jul. 11, 2017

(54) PLANT CULTIVATION METHOD

(71) Applicant: SYNGENTA PARTICIPATIONS AG, Basel (CH)

(72) Inventors: Jean-Marc Laine, Bruay-la-Buissiere (FR); Frederic Marie Devys, Lillers (FR)

(73) Assignee: Syngenta Participations AG, Basel (CH)

( * ) Notice: Subject to any disclaimer, the term of this patent is extended or adjusted under 35 U.S.C. 154(b) by 141 days.

This patent is subject to a terminal disclaimer.

(21) Appl. No.: 14/041,049

(22) Filed: Sep. 30, 2013

(65) Prior Publication Data

US 2014/0179000 A1   Jun. 26, 2014

Related U.S. Application Data

(63) Continuation of application No. 13/104,046, filed on May 10, 2011, now Pat. No. 8,574,908, which is a continuation of application No. 11/628,932, filed as application No. PCT/EP2005/006357 on Jun. 14, 2005, now Pat. No. 7,964,405.

(30) Foreign Application Priority Data

Jun. 15, 2004   (FR) ...................... 04 51184

(51) Int. Cl.
  *A01H 4/00*   (2006.01)
(52) U.S. Cl.
  CPC ............ *A01H 4/008* (2013.01); *A01H 4/005* (2013.01)
(58) Field of Classification Search
  None
  See application file for complete search history.

(56) References Cited

U.S. PATENT DOCUMENTS

| | | | |
|---|---|---|---|
| 5,514,580 A | 5/1996 | Oglevee-O'Donovan et al. | |
| 5,736,369 A | 4/1998 | Bowen et al. | |
| PP12,451 P2 | 3/2002 | Utecht | |
| 7,470,832 B2 * | 12/2008 | Kumar ................... | A01H 4/005 47/58.1 R |

FOREIGN PATENT DOCUMENTS

| | | |
|---|---|---|
| WO | 92/18617 | 10/1992 |
| WO | 2007/018252 A1 | 2/2007 |

OTHER PUBLICATIONS

Cassells et al. Plant and in vitro factors influencing the micropropagation of Pelargonium cultivars by bud-tip culture. Scientia Horticulturae, 21 (1983) 53-65.*
Evans. Methods in Molecular Biology, vol. 6, Plant Cell and Tissue Culture 1990, Chapter 10 Micropropagation Axillary Bud Multiplication, 93-103.*
Malaurie et al. The creation of an in vitro germplasm collection of yam (*Dioscorea* spp.) for genetic resources preservation. Duphytica 65: 113-122, 1993.*
Malaurie et al. Effect of growth regulators concentrations on morphological development of meristem-tips in Dioscorea cayenensis- D. rotundata complex and D. praehensilis. Plant Cell, Tissue and Organ Culture 41: 229-235, 1995.*
Perez-Tornero et al. Medium-term storage of apricot shoot tips in vitro by minimal growth method. HortScience 34(7):1277-1278, 1999.*
Viseur. Micropropagation of pear, Pyrus communis L., in a double-phase culture medium. Acta Horticulturae 212, 1987, 117-124.*
Cassells et al., Culture of Pelargonium hybrids form meristems and explants: chimeral and beneficially-infected varieties, Tissue Culture Methods for Plant Pathologists, 1980, 125-130.
Cassells et al., Plant and in vitro factors influencing the mciropropagation of Pelargonium cultivars by bud-tip culture. Scientia Horticulturae, 21, 1983, 53-65.
Cassells, Micropropagation of commerical Pelargonium species and hybrids (Glasshouse geraniums), Biotechnology in Agriculture and Forestry, vol. 20, 1995, 286-306.
Pliego-Alfaro et al., Propagation of avocado rootstocks by tissue culture, South African Avocado Growers' Association Yearbook, 1987, 10, 36-39.
Vinterhalter et al., Hormone-like effects of sucrose in plant in vitro culture, Phyton (Austria) Special issue: Plant Physiology, vol. 39, 1999, 57-60.
Viseur, Micropropagation of pear, *Pyrus communis* L., in a double phase culture medium, Acta Hortulturae, 212, 1987, 117-124.
Debergh et al., Acta Horticulturae, 1977, 78, 449-453.
Mithila et al., Plant Cell, Tissue and Organ Culture, 2001, 67, 1-9.
Grout, Methods in Molecular Biology, 1990, 111, 115-125 and 411-413.
Hassan, International Journal of Agriculture and Biology, 2004, 303-306.
Stamp et al., Plant Cell, Tissue and Organ Culture, 1990, 22, 127-133.
Roxas et al., J. Japan. Soc. Hort. Sci., 1995, 63, 4, 863-870.

* cited by examiner

*Primary Examiner* — June Hwu
(74) *Attorney, Agent, or Firm* — Dale Skalla

(57) ABSTRACT

A method for the production of young plants belonging to the group of herbaceous ornamentals, which method comprises an in vitro culture phase during which explants obtained from a parent stock of a species to be propagated, or derivatives of these explants, are subjected to micropropagation which is carried out under suitable conditions and on suitable culture media, in order to produce microplantlets which, when subjected to an in vivo culture phase, are intended to develop into a plant.

9 Claims, No Drawings

PLANT CULTIVATION METHOD

This application is a continuation of U.S. patent application Ser. No. 13/104,046 (U.S. Pat. No. 8,574,908), which is a continuation of U.S. patent application Ser. No. 11/628,932 (U.S. Pat. No. 7,964,405), which is National Phase entry of PCT/EP2005/006357, filed on Jun. 14, 2005, which claims priority to French Patent Application No. 0451184 filed on Jun. 15, 2004.

The present invention relates to a method for the production of young plants and/or of micro-parent stock of plants, but especially to plants belonging to the group of herbaceous ornamentals, which comprises an in vitro culture phase during which explants obtained from parent stock of plant species to be propagated, or derivatives of these explants, are subjected to one or more micropropagation cycles which are carried out under suitable conditions and on suitable culture media, in order to produce micro-plantlets which, when subjected to an in vivo culture phase, are intended to develop into plants or into micro-parent stock.

It is known that the in vitro micropropagation of a plant in the light results in an increased vegetative propagation rate by causing the maximum possible number of axillary buds of a plantlet maintained on a specific culture medium to break in order to develop shoots.

Methods for the production of plants which are based on an in vitro culture phase in the light and a subsequent in-vivo culture phase have been known to the skilled worker for a number of years already. It is recognized in the art that these methods have a number of advantages which is basically a result of going through an in vitro phase and which is reflected not only in terms of the quantities of plants produced per area, but also in terms of plant health, quality and final appearance of the plant. However, their use in horticulture is currently still greatly restricted since each type of plant grown requires specific culture conditions the development of which involves a great deal of time and effort and is therefore costly. The propagation rates that can be achieved with said methods are not yet sufficient to compensate for these disadvantages.

Moreover, it has been found that certain plant species such as, in particular, pelargonium, for which the production via this route has been attempted do not lend themselves readily to known micropropagation methods.

One of the objectives of the present invention is, therefore, to propose a process for the production of young plants and/or of micro-parent stock of plants which process is perfectly adapted to the culture of said plants, but especially of plants belonging to the group of herbaceous ornamentals such as, in particular, pelargonium, petunia including cascading petunia, poinsettia, cyclamen, chrysanthemum, busy Lizzie, verbena, or torenia, such as to achieve increased propagation rates.

Moreover, it is another objective of the invention to provide a method the application of which would make it possible to achieve proliferation rates, that are much higher than those obtained so far with methods wherein the proliferation phase is performed in the light.

Moreover, it is also an objective of the invention to propose a method for the production of young plants and/or of micro-parent stock of plants, but especially of plants belonging to the group of herbaceous ornamentals, which method integrates a particular in vitro micropropagation technique with the aid of which more vigorous young plants or parent stock with an exceptionally high branching rate and more rapid growth can be obtained.

Another object of the invention is to propose a vegetative propagation method which is suitable for ensuring the health status and the maintenance of genetic criteria, but especially genetic conformity of the plants over the generations, resulting in phenotypically uniform and properly synchronized plant populations.

The in vitro culture phase according to the present invention is also suitable for mechanization owing to the miniaturization of the cutting production that can be achieved by applying the method according to the present invention. Plants can be supplied in high density trays, which can be suitably used in automated transplanting systems involving transplanting robots.

Finally, the method, which is the subject of the present invention is also directed at improving the financial returns of the production of plants by reducing the time span and area required for their propagation by carrying out an in vitro micropropagation under specific conditions.

In one embodiment, the invention relates to a method for the production of young plants and/or of micro-parent stock of plants, but especially plants belonging to the group of herbaceous ornamentals, which method comprises an in vitro culture phase during which explants obtained from parent stock of species to be propagated, or derivatives of these explants, are subjected to a micropropagation phase, which is carried out under suitable conditions and on suitable culture media, in order to produce micro-plantlets which, when subjected to an in vivo culture phase, are intended to develop into plants or into micro-parent stock, characterized in that, to carry out said micropropagation:

(a) explants are obtained from parent stock of species to be propagated, or from derivatives of these explants,
(b) the explants are, under axenic conditions, placed on a shoot initiation medium which is composed such as to suit each plant species to be propagated, and, in the dark and for a suitable period of time, grown so that the formation of white filaments is induced which comprise axillary buds,
(c) optionally, each of the white filaments is then divided into a plurality of segments or pieces, each of which comprises an axillary bud,
(d) and the white filaments and/or pieces or segments thereof are, in the light, under axenic conditions and for a suitable period of time, placed into or on a rooting medium, which allows each axillary bud to produce a micro-plantlet which has roots.

In another embodiment, the method according to the invention, involving a micropropagation step, is characterized in that (a) explants are obtained from parent stock of species to be propagated, or from derivatives of these explants,
(b) the explants are, under axenic conditions, placed on a shoot initiation medium which is composed such as to suit each plant species to be propagated, and, in the dark and for a suitable period of time, grown so that the formation of white filaments is induced which comprise one or more axillary buds,
(c) optionally, each of the white filaments is then divided into a plurality of segments or pieces, each of which comprises an axillary bud, but at least one axillary bud,
(d) the white filaments and/or pieces or segments thereof obtained in step b) are, under axenic conditions transferred to a proliferation medium and grown in the dark for a suitable period of time sufficient to allow the tissue of the plant cuttings to multiply, preferably exponentially, and to produce a large quantity of etiolated white filaments comprising a high number of axillary nodes, which give rise to plantlets intended to develop during an "in vivo" phase if grown in light; or to develop into shoots with the axillary shoots becoming etiolated into white filaments, if grown in the dark, (e) this step (d) is repeated as often as necessary to produce different consecutive generations of white filaments until the desired amount of white filaments has been obtained, (f) and the white filaments or pieces thereof are, in the light, under axenic conditions and for a suitable period of time, placed into or on a rooting medium, which allows each axillary bud to produce a micro-plantlet which has roots.

The initiation medium used above in step (b) and the proliferation medium mentioned in step (d) may have an identical or an essentially identical composition or may be different media, depending on the requirements of the plant species or genotype used in the micropropagation method according to the invention.

Conditions and culture media that can be suitably used in plant micropropagation are well known to those skilled in the art of plant cultivation and are described, for example, in "Plant Propagation by Tissue Culture, Handbook and Directory of Commercial Laboratories, eds. Edwin F George and Paul D Sherrington, Exegetics Ltd, 1984".

In a further aspect of the present method, a traditional culture medium, but especially a culture medium of the "MS" type, either supplemented only with a compound which belongs to the cytokinin family of growth regulators or supplemented with a compound which belongs to the cytokinin family of growth regulators and with a compound which belongs to the auxin family of growth regulators is used as an initiation and/or a proliferation medium in the micropropagation phase. Said growth regulating compounds are specifically chosen and provided in the medium in a concentration, which promotes proliferation of the plant material from the plant species to be multiplied, but especially the development of white filaments from the axillary buds or nodes initially present on the explant material and elongation growth of said white filaments such that a maximum number of axillary buds/per initial bud or node are produced on the developing filaments, but at least between 2 and 10 axillary buds/per initial bud, specifically between 3 and 7 axillary buds/per initial bud, but especially between 4 and 5 axillary buds/per initial bud, sustaining a high multiplication rate.

Compounds which belong to the cytokinin family of growth regulators and which may be used in the method according to the present invention as a suitable supplement for the initiation and/or proliferation medium may be any compound selected from the group consisting of purin-based cytokinins such as, for example, kinetin, zeatin, 6-benzylamino purine (BAP); 6-(benzylamino)-9-(2-tetrahydropyranyl0-9h-purine (PBA); or (6-(γ,γ-dimethylallylamino) purine (2iP); and cytokinins based on substituted phenyl ureas such as, for example, thidiazuron (TDZ) or any other compound belonging to the cytokinin family of growth regulators which is know or demonstrated to be suitable for directly or indirectly promoting the propagation potential of the plant species to be multiplied, but especially the development of white filaments from the axillary buds or nodes initially present on the explant material and elongation growth of the developing white filaments such that a maximum number of axillary buds/per initial bud or node are produced on the developing filaments, but at least between 2 and 10 axillary buds/per initial bud, specifically between 3 and 7 axillary buds/per initial bud, but especially between 4 and 5 axillary buds/per initial bud, sustaining a high multiplication rate.

Compounds which belong to the auxin family of growth regulators and which may be used in the method according to the present invention as a suitable supplement for the initiation and/or proliferation medium may be any compound selected from the group consisting of indole-3-butyric acid (IBA); α-naphthaleneacetic acid (NAA); indole-3-acetic-acid (IAA); and 2,4-dichlorophenoxyacetic acid (2,4-D) or any other compound belonging to the auxin family of growth regulators which is know or demonstrated to be suitable for directly or indirectly promoting the propagation potential of the plant species to be multiplied, but especially the development of white filaments from the axillary buds or nodes initially present on the explant material and elongation growth of said white filaments such that a maximum number of axillary buds/per initial bud or node are produced on the developing filaments, but at least between 2 and 10 axillary buds/per initial bud, specifically between 3 and 7 axillary buds/per initial bud, but especially between 4 and 5 axillary buds/per initial bud, sustaining a high multiplication rate.

Further compounds that may be suitably used as a supplement for the initiation and/or proliferation medium are, for example, inositol, but especially one or more of its nine distinct isomers commonly found in plant and/or animal systems, such as myo-inositol, further, biotine, folic acid, cystein or polyvinyl pyrrolidone (PVP) or any other compound which is know or demonstrated to directly or indirectly support growth and/or the propagation of the plant species to be multiplied.

Another compound that may be used as a supplement in the propagation medium according to the invention is a suitable carbon source, especially a sugar compound such as, for example, sucrose or glucose or any other sugar compound commonly used in plant cultivation or a combination thereof.

Yet, the present method is further characterized by the fact that white filaments are obtained comprising axillary buds and that said first generation of white filaments, but especially segments or pieces of said filaments obtainable through, for example, cutting of the filaments into a plurality of defined pieces or segments containing at least one axillary bud, are returned under axenic conditions and in the dark to a fresh proliferation medium and cultivated in the dark for a suitable period of time so as to induce the formation of a new generation of white filaments such that a maximum number of axillary buds/per initial bud present on the first generation filament are produced on the developing filaments, but at least between 2 and 10 axillary buds/per initial bud, specifically between 3 and 7 axillary buds/per initial bud, but especially between 4 and 5 axillary buds/per initial bud, sustaining a high multiplication rate. The procedure may be repeated as often as necessary to produce different consecutive generations of white filaments until the desired amount of white filaments has been obtained. Thus, the present invention makes it advantageously possible to propose a technique which can be defined for a given plant species, in particular a plant species belonging to the group of herbaceous ornamentals by a sequence of standardized operations in which the type of the media and the culture conditions may, if required, be specifically adapted to suit varieties or groups of varieties within said species in order to increase the vegetative propagation rate and maintain this high propagation rate over one or more, specifically over up to 10, more specifically over up to 5, propagation cycles in the dark.

Plants that can be used in a process according to the present invention are plants that belong to the group of herbaceous ornamentals such as plants of the families Adiantaceae Amaranthaceae, Amaryllidaceae, Apiaceae, Apocynaceae, Araceae, Araliaceae, Asclepiadaceae, Aspleniaceae, Asteraceae, Athyriaceae, Balsaminaceae, Begoniaceae, Buxaceae; Campanulaceae, Cannaceae, Carophyllaceae, Crassulaceae, Dryopteridaceae, Euphorbiaceae, Fumariaceae, Geraniaceae, Hyperaceae, Iridaceae, Lamiaceae, Liliaceae, Lobeliaceae; Nyctaginaceae, Osmundaceae, Piperaceae, Plumbaginaceae, Poaceae, Portulacaceae, Ranunculaceae, Rosaceae, Saururaceae, Saxifragaceae, Scrophulariaceae, Solanaceae, Verbenaceae, and Violaceae, in particular, plants belonging to the group of pelargonium, petunia including cascading petunia, poinsettia, cyclamen, chrysanthemum, busy Lizzie, verbena, or torenia, but especially pelargonium.

In one embodiment of the present invention, implementation of the present method results in a first variant wherein, in order to obtain bacteria- and virus-free parent stock, meristems, specifically growing meristems, but especially shoot meristems, are taken from parent stock and used as explants which are grown under axenic conditions in the light for a first period of time on a development medium common to each plant variety, sufficient to bring about the formation of little plantlets which have first leaf primordia and then, for a second period of time, on or in a rooting medium common to each plant variety, in order to obtain rooted plantlets which are free from bacteria and viruses and which are intended to be placed on a shoot initiation medium in the dark in order to produce said white filaments according to the invention.

Conditions and culture media that can be suitably used in plant meristem culture as well as for rooting plantlets obtained by said culture are well known to those skilled in the art of plant cultivation and are described, for example, in "Plant Propagation by Tissue Culture, Handbook and Directory of Commercial Laboratories, eds. Edwin F George and Paul D Sherrington, Exegetics Ltd, 1984".

In this situation, according to a characteristic of the present method, the volume of the rooting medium used is supplemented in a suitable manner during the rooting phase of said plantlets. Rooted plantlets are then transferred to soil or any other suitable supporting medium commonly employed in plant cultivation practice for growing young plants, acclimatized to changed environmental conditions such as those present in a greenhouse and grown there for a suitable time period, but at least for 4 weeks to 10 weeks, especially for 5 weeks to 6 weeks.

The plants may then be subjected to a suitable testing system in order to detect and discard plant material that is infected with viral and/or bacterial pathogens such as, for example, an "ELISA"-type test and any samples which test positive are eliminated, while those which test negative are retained as bacteria- and virus-free parent stock and used as a source of explants.

In one embodiment of the invention, the leaves and roots of said plantlets are suppressed for a suitable period of time before being placed, under axenic conditions and in the dark, on a shoot initiation medium which is specific to each variety in order to produce said white filaments.

In another embodiment of the invention, micro-cuttings are taken from the bacteria- and virus-free parent stock plants obtainable through a meristem culture as described hereinbefore and used as explants. Alternatively, certified bacteria- and virus-free parent stock that may be purchased from a commercial source may be used for obtaining micro-cuttings. In particular, branches, but especially shoot tips comprising one or more axillary buds are taken and cut into pieces with each piece containing at least one bud.

In accordance with a specific embodiment of the invention, the leaves and the stipules of the apical portion of the micro-cuttings are suppressed for a suitable period of time before being placed, under axenic conditions and in the dark, on a shoot initiation medium which is specific for each plant variety, in order to produce said white filaments.

In accordance with another advantageous characteristic of the present method, the white filaments which have axillary buds may be stored for a given period of time before the rooting phase during which each bud produces a rooted micro-parent stock plant which is intended for being cultured in vivo.

Secondly, the present invention also relates to the micro-plantlets, young plants and micro-parent stock obtained by carrying out the method as defined hereinabove.

In a specific embodiment, the present invention relates to young plants which are distinguished in particular by an increased branching rate, rapid growth, compact foliage, auto-regulation of the plant, but especially to young plants selected from the group consisting of pelargonium, petunia including cascading petunia, poinsettia, cyclamen, chrysanthemum, busy Lizzie, verbena, and torenia.

The present invention also relates to the characteristics which will be seen from the description to follow, and which must be considered in isolation or in accordance with any possible combinations thereof.

The method according to the invention comprises an "in vitro" culture phase during which plant tissues are, under axenic conditions, subjected to different treatments, in particular of micropropagation, which treatments are carried out under specific conditions to make these plant tissues multiply exponentially and produce a large quantity of plantlets which are intended to develop during an "in vivo" phase, either directly into plants or into micro-parent stock intended to act itself as starting material for obtaining plants.

The method according to the invention is further expected to be suitable for being applied either to plantlets obtained from meristems taken from any parent stock, or to micro-cuttings taken from healthy parent stock, viz. certified, bacteria- or virus-free parent stock.

Thus, the variant of the method which relies on the use of meristems and which has the advantage of leading to a sanitization of parent stock which may be attacked by any pathogen requires supplementary steps of obtaining plantlets. To this end, meristems, but especially developed meristems with the first leaf primordia are obtained and first grown for a period of approximately 4 months in the light in a suitable container such as, for example, a Petri dish, glass jar or pot, on a development medium whose composition is advantageously common to all the plant species to which the present method relates, for example, one of the traditionally used plant cultivation media such as, for example, a "MS"-type culture medium (MS macro- and micro-elements; MS vitamins) which is supplemented with compounds which belong to the cytokinin family of growth regulators.

Small plantlets obtained from the developed meristems, are subsequently placed on or in a rooting medium whose composition is identical, whatever the plant species, preferably a rooting medium traditionally used in plant cultivation such as, for example, a culture medium of the "MS"-type, in the light, to obtain small plantlets, which, approximately after one month, are transferred to a suitable container such as, for example, a glass jar or glass pot, which allows the root volume to increase. To further promote root development ventilated container may be used.

After this procedure, rooted plantlets are obtained which are ready to enter the actual in vitro micropropagation phase, in the same way as the micro-cuttings taken from healthy parent stock such as, for example, certified mother stock plants grown in the greenhouse under controlled phytosanitary conditions.

In a specific embodiment of the invention, the plantlets or micro-cuttings are, before being subjected to a micropropagation treatment, first rejuvenated by, for example, suppressing the roots and the leaves and then placed on a shoot initiation medium which is developed specifically to suit the plant variety to be propagated and which is spread out in a suitable container such as a Petri dish.

In particular, leafs and, if present, roots are removed from the stem or branches of the plant to be micropropagated and, preferably, surface sterilized. They are then cut into pieces or segments with each piece or segment containing at least one node or axillary bud. The cuttings are transferred on to a shoot initiation medium and cultivated in the dark under conditions and for a period of time, which allow the plant cuttings to multiply and produce a large quantity of etiolated while filaments comprising a high number of axillary nodes, which give rise to plantlets intended to develop during an "in vivo" phase if grown in light; or to develop shoots with the axillary shoots becoming etiolated into white filaments, if grown in the dark.

The cultivation in the dark of plant cuttings as well as cuttings obtained from etiolated white filaments comprising at least one axillary bud or node is carried out for a period of time sufficient to allow for the axillary nodes or axillary buds to develop into shoots and the axillary shoots to become etiolated into white filaments comprising axillary buds, with the number of axillary buds produced on the developing filaments amounting to at least between 2 and 10 axillary buds/per initial node present in the cutting, specifically between 3 and 7 axillary buds/per initial node present in the cutting, but especially between 4 and 5 axillary buds/per initial node present in the cutting, but at least for a period of between approximately 2 weeks to approximately 12 weeks, specifically of between approximately 3 weeks to approximately 7 weeks, more specifically of between approximately 4 weeks to approximately 5 weeks, but especially of approximately 4 weeks.

In a specific embodiment, for shoot initiation and maintenance the plant explants are placed horizontally on the cultivation medium and grown under conditions, which forces the developing shoots to grow essentially horizontally. This can be achieved by growing the explants in a container such as a Petri dish, which is designed such as to prevent the explant from growing vertically owing to space limitations in the vertical direction. For the developing shoots it is preferable to be in close contact with the cultivation medium and to establish more than just one contact point with the medium during micropropagation.

In accordance with the present method, it is advantageous to use an initiation and/or a proliferation medium which has substantially the same basic composition as the above-mentioned development medium and rooting medium, namely a composition based on the traditional presence of macro- and micro-elements and vitamins such as, for example, those present in the commonly used MS media.

The composition and concentration of the macro- and micro-elements and vitamins within said media may vary to a certain extent depending on the plant species or genotype involved. Such minor adaptations are well within the skills of the skilled artisan in the area of plant cultivation and part of his routine optimization work. For example, when using an MS-type medium it has proven advantageous in some instances to employ reduced concentrations of macro- and/or micro-elements and/or vitamins, especially a concentration which establishes itself somewhere between a full-strength and a half-strength concentration, but in particular, a half-strength concentration.

Said basic composition may be further supplemented by the addition of compounds belonging to the cytokinin family of growth regulators or by the simultaneous addition of compounds belonging to the cytokinin family of growth regulators and compounds belonging to the auxin family of growth regulators, depending on the plant species to be propagated, which compounds support shoot multiplication by promoting the breakage and development of axillary buds into etiolated shoots and further into white filaments and/or the growth, but especially the elongation growth of the developing shoots into shoots comprising a high number of axillary nodes.

In a specific embodiment, a two-layer cultivation approach is employed in the method according to the invention wherein the plant cultivation medium is provided in form of a two layer system comprising a solidified bottom layer comprising essentially macro- and micro-elements, vitamins and a carbon source as described herein below, but no growth regulator, which is overlayed with a fluid top layer comprising a growth regulator, especially a growth regulator belonging to the cytokinin family of growth regulators or a combination of growth regulators belonging to the cytokinin family of growth regulators and to the auxin family of growth regulators, depending on the plant species to be propagated, which growth regulators support shoot multiplication by promoting the breakage and development of axillary buds into etiolated shoots (white filaments) and/or the growth, but especially the elongation growth of the developing shoots into shoots comprising a high number of axillary nodes.

The fluid top layer may, in addition to the growth regulators belonging to the cytokinin and/or the auxin family of growth regulators of growth regulators, contain other growth regulators of a different family of growth regulators such as, for example, growth regulators belonging to the gibberellin family of growth regulators, which are known to promote shoot elongation.

The fluid top layer may further contain compounds supporting growth of the developing shoot such as, for example, macro- and micro-elements, vitamins and a carbon source. The volume of the fluid top layer as compared to the solid bottom layer amounts to between about 1% and about 10%, specifically between about 2% and about 7%, more specifically between about 3% and about 5%, but especially between about 3% and about 4%.

In a specific embodiment of the invention, the two layer cultivation is carried out in a suitable container commonly used in plant cultivation such as, for example, a glass jar or glass pot with a size big enough to allow the developing white filaments to grow properly. The containers may, in addition, be ventilated in order to support growth and development of the white filaments.

Compounds which belong to the cytokinin family of growth regulators and which may be used in the method according to the present invention as a suitable supplement for the initiation and/or proliferation medium may be any compound selected from the group consisting of kinetin, zeatin, 6-benzylamino purine (BAP); 6-(benzylamino)-9-(2-tetrahydropyranyl0-9h-purine (PBA); (6-(γ,γ-dimethylallylamino) purine (2iP); and thidiazuron (TDZ) or any other compound belonging to the cytokinin family of growth regulators which is know or demonstrated to be suitable for propagation of the plant species to be multiplied.

Compounds belonging to the cytokinin family of growth regulators are offered in the initiation and/or proliferation medium according to the invention in a concentration of between 0.01 mg/l and 5.0 mg/l-7.0 mg/l, specifically between 0.03 and 2.0 mg/l, more specifically between 0.04 and 1.0 mg/l, but especially between 0.05 and 0.5 mg/l.

Adaptations may need to be made within the above defined ranges in order to accommodate the specific needs of the plant species to be multiplied.

Compounds which belong to the auxin family of growth regulators and which may be used in the method according to the present invention as a suitable supplement for the initiation and/or proliferation medium may be any compound selected from the group consisting of indole-3-butyric acid (IBA); α-naphthaleneacetic acid (NAA); indole-3-acetic-acid (IAA); and 2,4-dichlorophenoxyacetic acid (2,4-D) or any other compound belonging to the auxin family of growth regulators which is know or demonstrated to be suitable for propagation of the plant species to be multiplied.

Compounds belonging to the auxin family of growth regulators are offered in the initiation and/or proliferation medium according to the invention in a concentration of between 0.01 mg/l and 5.0 mg/l, specifically between 0.03 and 2.0 mg/l, more specifically between 0.04 and 1.0 mg/l, but especially between 0.05 and 0.5 mg/l.

Adaptations may need to be made within the above defined ranges in order to accommodate the specific needs of the plant species to be multiplied.

Some of the growth promoting substances such as compounds belonging to the group of the substituted phenyl ureas, for example thidiazuron (TDZ), alone or in combination with another compound of the cytokinin family of growth regulators such as, for example, 6-benzylamino purine (BAP) are known to be potent stimulators of multiple shoot formation. These substances are further known to be rather persistent and highly active already at low concentrations in a range of between 0.001 mg/l and 0.1 mg/l but may, in some cases, cause some undesirable effects like, for example, organ aberrations or stunted shoot growth.

These undesired effects may be compensated for by the addition of a gibberellin-type growth regulator such as gibberellic acid, which promotes shoot elongation.

Another possibility to avoid undesired effects caused by the presence of growth regulators, but especially growth regulators which may negatively affect shoot growth and elongation such as, for example, TDZ, in the initiation and/or the proliferation medium, is the application of a two-layer cultivation approach as mentioned hereinbefore, whereby the compounds belonging to the group of the substituted phenyl ureas such as, for example, thidiazuron (TDZ), alone or in combination with another compound of the cytokinin family of growth regulators such as, for example, 6-benzylamino purine (BAP) are only present in the fluid top layer in a concentration high enough to promote shoot multiplication but low enough to prevent any undesired effects to occur, but specifically in a concentration of approximately between 0.001 mg/l and 2.0 mg/l, more specifically between approximately 0.005 and 1.0 mg/l, but especially between 0.01 and 0.1 mg/ml.

Further compounds that may be suitably used as a supplement for the initiation and/or proliferation medium are, for example, inositol, but at least one of its nine distinct isomers such as myo-inositol, further, biotine, folic acid, cystein or polyvinyl pyrrolidone (PVP) or any other compound which is know or demonstrated to directly or indirectly promote growth and/or the propagation potential of the plant species to be multiplied.

Another compound that may be used as a supplement in the propagation medium according to the invention is a suitable carbon source, especially a sugar compound such as, for example, sucrose or glucose, or any other sugar compound commonly used in plant cultivation, or a combination thereof.

The white filaments obtained in this or any further propagation cycles can be placed in the dark under conditions that allow preservation of the filaments for later rooting or as stock for further propagation rounds. For example, filaments stored at a temperature of between 2° C. and 10° C., specifically of between 3° C. and 8° C., but especially of between 4° C. and 6° C. may be stored for at least up to 10 month, specifically for at least up to 7 month, but especially for at least up to 5 months.

Thus, the micropropagation phase can advantageously be carried out again, as often as necessary in cycles of between approximately 3 weeks to 12 weeks, specifically of between approximately 4 weeks to 6 weeks, but especially of between approximately 4 weeks to 5 weeks, in order to obtain large quantities of white filaments.

In accordance with a further characteristic of the present method, which allows the quality of the plants produced to be ensured in terms of health, plants resulting from the cultivation of meristems and/or the white filaments are subjected to a suitable testing system such as, for example, an "ELISA"-type test and any samples which test positive are eliminated, while those which test negative are retained.

Secondly, in accordance with another advantageous characteristic, it is possible to store for as long as necessary the portions of white filaments in the dark at ambient temperature on a proliferation medium which is replaced periodically, before the rooting phase during which each bud produces a rooted micro-plantlet which is intended for culturing in vivo.

Several plant species have already been subjected to a micropropagation treatment in accordance with the method of the present invention.

Thus, it has been possible to demonstrate that, by using a medium of the traditional "MS"-type supplemented with cytokinins or a combination of cytokinins and auxins as a shoot initiation and a proliferation medium, micro-plantlets of pelargonium, for example, of zonal geranium, of double ivy-leaved geranium, or of simple ivy-leaved geranium, as well as petunia and osteospermum micro-plantlets have successfully been produced.

Moreover, the method according to the invention can also be applied to other plant species belonging to the group of herbaceous ornamentals such as, for example, plants of petunia including cascading petunia, kalanchoe, torenia, verbena and rose-bush to successfully produce micro-plantlets.

Moreover, by applying the method according to the invention it has also been found that the young plants or micro-parent stock obtained from micro-plantlets had particularly interesting characteristics.

The plants produced through this method naturally present a very high degree of branching, rapid rooting, homogeneous growth in terms of volume, rapid hardening-off of the plant, a leaf area which is smaller than that of plants obtained in traditional culture methods, and a pronounced juvenile character, which can be seen in particular from micro-plantlets of zonal geranium, a micro-parent stock of zonal geranium and a micro-parent stock plant of cascading petunia, respectively.

The present method also offers an advantageous solution which makes possible an improved productivity and flexibility in the production process as compared with the traditional culture techniques, in particular by reducing the surfaces which are traditionally allocated to the culture of parent stock by a factor of four.

Moreover, by applying the method according to the invention it would be possible to achieve proliferation rates, that are much higher than those obtained so far performing the proliferation phase in the light. If one assumes that each white filament obtained from a starting plantlet is able to provide at least five axillary buds per month, which, themselves, are capable of providing five rooted micro-plantlets, each of which, in turn, is capable of providing five white filaments per month, this would lead, after 9 micropropagation cycles of one month, to approximately 2 million plants obtained from a single starting plantlet.

Moreover, the implementation of the present method further offers many advantages which are reflected in the different horticultural networks concerned, in particular, in an improvement of the administration of orders, and in the higher plant quality.

Although the invention has been described with reference to a particular embodiment, it is well understood that it is in no way limited thereto and that various modifications of form, materials and combinations of these various elements can be made thereto without, however, departing from the scope or the spirit of the invention.

The following working examples refer to examples of implementing the present method, which are given by way of illustration and not by way of limitation and which relate to the production of pelargonium, petunia and osteospemum plants, more specifically to the production of plants which belong to different varieties or genotypes of pelargonium, petunia and osteospemum.

EXAMPLES

Example 1

Petunia 1.1 Plant Material and Etiolation

Petunia certified motherstock plants are grown in the greenhouse for at least 6 weeks under controlled phytosanitary conditions. Branches are obtained from said motherstock plants and used as explants for shoot multiplication and etiolation.

All the leaves are removed from the branches and the defoliated branches are surface sterilized with a 1.3% sodium hypochlorite solution (30% commercial bleach) for 10 minutes and washed three times with sterile distilled water.

After sterilization, the defoliated branches are cut into pieces under axenic conditions with each piece containing one or two nodes.

Explants are placed horizontally on a solidified shoot initiation medium in a petridish, with a maximum of three explants per petridish. Petridishes are sealed with nescofilm.

For etiolation two MS-based media are used for shoot initiation, MS1 and MS1-2. The two media essentially differ in the concentration of the MS macro elements in that the MS1-2 medium contains the macro elements only in half-strength concentration. Both media can be used for shoot initiation and etiolation of Petunia explants, even though certain genotypes appear to have preferences for one or the other medium.

The MS1 medium contains MS micro salts+MS macro salts+MS vitamins, sucrose as a carbon source, myo-inositol, biotin, and folic acid as additional, non-MS vitamins, PVP (polyvinyl pyrrolidone) as a further supplement and BAP (6-benzylaminopurine) and 2iP (2-isopentenyl-adenine) as growth hormones of the cytokinin family of growth regulators. The medium is solidified with plant agar. The pH is set at 5.8 before autoclaving (for further details of the medium composition see table A below).

The M1-2 medium contains half strength MS macro salts+full MS micro salts and MS vitamins, sucrose as a carbon source, myo-inositol, biotin, and folic acid as additional, non-MS vitamins, PVP (polyvinyl pyrrolidone) as a further supplement and BA (6-benzylaminopurine) and 2iP (2-isopentenyl-adenine) as growth hormones of the cytokinin family of growth regulators. The medium is solidified with plant agar. The pH is set at 5.8 before autoclaving (for further details of the medium composition see table A below).

Explants are grown in the dark for 4 weeks at a temperature of between 18° C. and 20° C. In general 60%-90% of the explants will form filaments (see table 1 below).

After four to five weeks cultivation in the dark the axillary shoots are etiolated into white filaments. Each filament has one or more axillary nodes.

TABLE 1

| Number of filaments per explant after 4 weeks | | |
|---|---|---|
| genotype | MS1 | MS1-2 |
| A971-1 | 3.0 | 5.0 |
| A895-3 | 4.5 | 8.0 |
| A1019-1 | — | 6.2 |
| A938-5 | 5.0 | 1.0 |
| A1010-3 | 5.0 | 17.0 |
| A948-1 | 6.0 | 10 |
| average | 3.9 | 7.9 |

1.2 Proliferation

For maintenance, the white filaments obtained in Example 1.1 are cut into pieces containing one or two axillary nodes and transferred to fresh MS1 or MS1-2 medium in petridishes. For preserving the stock the petridishes can be placed in the dark at 4° C. for at least 4 months.

For an efficient proliferation filaments are used which contain more than one axillary node. However, satisfactory results could also be obtained with filaments containing only one axillary node as the starting material.

The filaments or pieces thereof obtained through cutting of the filaments comprising between 2 and 6 axillary nodes are grown in glass jars containing 66 ml medium. The medium is SP1, which contains modified MS macro salts, MS micro salts+MS vitamins, sucrose as the carbon source, myo-inositol, biotin, folic acid as additional non-MS vitamins, BAP (6-benzylaminopurine) as a representative of the cytokinin family of growth regulators, and IAA (Indole-3-Acetic Acid) as a representative of the auxin family of growth regulators. The medium is solidified with plant agar (for further details of the medium composition see table A below).

6 filaments or pieces thereof are placed in one jar, with the first node just below the surface of the agar. The jars are placed in the dark at a temperature of between 18° C. and 22° C. for 5-6 weeks. After five to eight weeks further subcultivation cycles can be carried out by following essentially the same procedure as described above.

At each subculture the proliferation rate or multiplication rate can be determined by dividing the number of filaments formed (after separating or cutting the tissue back to the original number of nodes) by the initial number of filaments. The proliferation rates are determined for 6 genotypes for 2 consecutive subcultures of between 4 to 5 weeks (see table 2 below).

TABLE 2

Proliferation rates of genotypes

| subculture | 1 | 2 |
|---|---|---|
| A971-1 | 7.0 | 5.5 |
| A895-3 | 3.0 | 4.8 |
| A1019-1 | 3.0 | 4.2 |
| A938-5 | 1.0 | 5.8 |
| A1010-3 | 2.0 | 1.4 |
| A948-1 | 3.5 | 8.0 |
| average | 3.3 | 5.0 |

1.3 Rooting

For rooting smaller explants are used. Each filament contains one or two axillary nodes. The explants are transferred to ventilated containers (ecoline boxes with XXL filter). The rooting medium is MS0-2 (half strength MS macro salts, full strength MS micro salts and MS vitamins, sucrose as the carbon source, myo-inositol, biotin, folic acid as additional non-MS vitamins, and plant agar as the solidifying agent) or RAI2-2 (half strength MS macro salts, full strength MS micro salts and MS vitamins, sucrose as the carbon source, myo-inositol, biotin, folic acid as additional non-MS vitamins, indole-acetic acid, indole-butyric acid as growth regulators of the auxin family of growth regulators, and plant agar as the solidifying agent).

Both media can be used and will give similar results. Plants are rooted for four weeks at a temperature of between 18° C. and 22° C. in a 16 h photoperiod of app. 3000 lux. Rooting percentages are determined after 4-6 weeks.

The rooted plantlets are taken out of the containers and washed in water to remove traces of medium and agar. The plantlets are transferred to soil in the greenhouse at 20° C. where they acclimatized and are treated as normal tissue culture plants.

Example 2

Osteospermum 2.1. Plant Material and Etiolation

Osteospermum certified motherstock plants are grown in the greenhouse for at least 6 weeks under controlled phytosanitary conditions. Branches are obtained from said motherstock plants and used as explants for shoot multiplication and etiolation.

All the leaves are removed from the branches and the defoliated branches are surface sterilized with a 1.3% sodium hypochlorite solution (30% commercial bleach) for 10 minutes and washed three times with sterile distilled water.

After sterilization, the defoliated branches are cut into pieces under axenic conditions, with each piece containing one or two axillary nodes. Explants are placed horizontally on a solidified shoot initiation medium in a petridish, with a maximum of two explants per petridish. Petridishes are sealed with nescofilm.

For etiolation two MS-based media are used, MS1-2 and MS2Z, which essentially differed in the concentration of the MS macro elements and the growth hormone composition. Both media can be used for etiolation of Osteospermum explants, even though certain genotypes appear to have preferences for one or the other medium.

The M1-2 medium contains half strength MS macro salts+full strength MS micro salts and MS vitamins, sucrose as a carbon source, myo-inositol, biotin, and folic acid as additional vitamins, PVP (polyvinyl pyrrolidone) as a further supplement, and BAP (6-benzylaminopurine), and 2iP (2-isopentenyl-adenine) as representatives of growth factors of the cytokinin family of growth regulators. The medium is solidified by addition of plant agar. The pH is set at 5.8 before autoclaving (for further details of the medium composition see table A below).

The MS2Z medium contains full strength MS micro+MS macro salts+MS vitamins, sucrose as a carbon source, myo-inositol, biotin, and folic acid as additional non-MS vitamins, and zeatine as the growth factor of the cytokine family of growth regulators. The medium is solidified by addition of plant agar. The pH is set at 5.8 before autoclaving (for further details of the medium composition see table A below).

Explants are grown in the dark at a temperature of 18° C. (see table 3 below). After four weeks of cultivation in the dark the axillary shoots are etiolated into white filaments. Each filament has one or more axillary nodes.

TABLE 3

Number of filaments per explant after 4 weeks

| genotype | MS1-2 | MS2Z |
|---|---|---|
| E192-1 | 0.75 | 0 |
| D209-3 | 0 | 0 |
| E207-2 | 3.3 | 2.2 |
| E206-1 | 0.6 | 0.3 |
| average | 1.2 | 0.6 |

2.2 Proliferation 2.2.1 Single Layer Cultivation

The white filaments obtained in Example 2.1 are cut into pieces containing one or two nodes and transferred to fresh MS1-2 in petridishes for maintenance after four-five weeks. For preserving the stock the petridishes can be placed in the dark at 4° C. for at least 4 months.

For an efficient proliferation filaments are used which contain at least two axillary nodes. The further steps are essentially carried out as described in Example 1.2 for Petunia.

TABLE 4

Proliferation rate of filaments after 4 weeks in petridishes

| genotype | Sub 1 | Sub2 |
|---|---|---|
| E192-1 | 1.0 | 4.7 |
| D209-3 | 0.8 | 4.3 |
| E207-2 | 4.8 | 6.5 |
| E206-1 | 5.5 | 4.5 |
| average | 3.0 | 5.0 |

2.2.2 Double-Layer Cultivation

In a second experiment the white filaments or pieces thereof obtained through cutting and comprising at least 2 axillary nodes are grown in glass jars containing 66 ml medium. The medium is MS0, which contains MS micro+

MS macro salts+MS vitamins, sucrose as the carbon source, myo-inositol, biotin, folic acid as additional, non MS vitamins and plant agar as a solidifying agent (for further details of the medium composition see table A below).

About 5 filaments are placed in one jar, with the first node just below the surface of the agar. Then 2 ml liquid medium B1 (MS micro+MS macro salts+MS vitamins, sucrose as the carbon source, myo-inositol, biotin, folic acid as additional, non MS vitamins, and zeatin and BAP (6-benzylaminopurine) as growth regulators of the cytokinin family of growth regulators (for further details of the medium composition see table A below)) is added on top of the solid medium. For 100 ml of solid medium 3 ml liquid B1 will be used. The jars are placed in the dark at 18-22° C. for five weeks At each subculture the proliferation rate or multiplication rate can be determined by dividing the number of filaments formed (after separating or cutting the tissue back to the original number of nodes) by the initial number of filaments.

2.3 Rooting

For rooting smaller explants are used. Each filament contains one or two axillary nodes. The explants are transferred to ventilated containers (ecoline boxes with XXL filter). The rooting medium is MS0-2 (half strength MS macro salts, full strength MS micro salts and MS vitamins, sucrose as the carbon source, myo-inositol, biotin, folic acid as additional non-MS vitamins, and plant agar as the solidifying agens) or RAI2-2 (half strength MS macro salts, full strength MS micro salts and MS vitamins, sucrose as the carbon source, myo-inositol, biotin, folic acid as additional non-MS vitamins, indole-acetic acid, indole-butyric acid as growth regulators of the auxin family of growth regulators, and plant agar as the solidifying agens).

Both media can be used and will give similar results. Plants are rooted for four weeks at a temperature of between 18° C. and 22° C. in a 16 h photoperiod of app. 3000 lux. Rooting percentages are determined after 4-6 weeks.

The rooted plantlets are taken out of the containers and washed in water to remove traces of medium and agar. The plantlets are transferred to soil in the greenhouse at 20° C. where they acclimatized and are treated as normal tissue culture plants.

Example 3

Pelargonium 3.1 Plant Material and Etiolation

Pelargonium certified motherstock plants are grown in the greenhouse for at least 6 weeks under controlled phytosanitary conditions. Branches are obtained from said motherstock plants and used as explants for etiolation. Before sterilization all the leaves are removed. The explants are surface sterilized with a 1.3% sodium hypochlorite solution (30% commercial bleach) for 15 minutes and washed three times with sterile distilled water.

The defoliated and sterilized branches are cut into pieces such that each resulting piece contains one or two nodes. Explants are placed horizontally on medium in a petridish, with a maximum of three explants per petridish. Petridishes are sealed with nescofilm.

For shoot multiplication and etiolation two different MS-based media (MS1 and MS2Z) are used. Both media can be suitably used for the shoot multiplication and etiolation of the Pelargonium explants. Certain of the tested genotypes appear to have preferences for one or the other medium, however, overall the results obtained are very similar for both media.

The MS1 medium contains MS micro+MS macro salts+MS vitamins, sucrose as a carbon source, myo-inositol, biotin, folic acid as additional, non MS-vitamins, PVP (polyvinyl pyrrolidone) as a further supplement, BAP (6-benzylaminopurine), and 2iP (2-isopentenyl-adenine) as growth regulators of the cytokinin family of growth regulators and plant agar as a solidifying agent. The pH is set at 5.8 before autoclaving (for further details of the medium composition see table A below).

The MS2Z medium contains MS micro+MS macro salts+MS vitamins, sucrose as a carbon source, myo-inositol, biotin, folic acid as additional, non MS-vitamins, zeatine as a growth regulator of the cytokinin family of growth regulators and plant agar as the solidifying agent. The pH is set at 5.8 before autoclaving (for further details of the medium composition see table A below).

Explants are grown in the dark at a temperature of between 22° C. and 24° C. for 3 to 4 weeks. In general 60%-80% of the explants will form a filament.

After three to four weeks in the dark the axillary shoots are etiolated into white filaments. Each filament had one or more axillary nodes.

3.2 Proliferation

The white filaments obtained in Example 3.1 are transferred to fresh MS1 or MS2Z medium in petridishes for maintenance. They are cut into pieces containing one or two nodes. For preserving the stock the petridishes can be placed in the dark at 4° C. for at least 4 months.

For an efficient proliferation each filament or pieces thereof obtained through cutting contain at least two or three, but preferably four axillary nodes at the start of the subculture. The filaments are grown in glass jars containing 66 ml medium. The medium is MS0, which contain MS micro+MS macro salts+MS vitamins, sucrose as a carbon source, myo-inositol, biotin, folic acid as additional non-MS vitamins, and plant agar as the solidifying agent (for further details of the medium composition see table A below).

About 15±5 filaments are placed in one jar, with the first node just below the surface of the agar. Then 2 ml liquid medium KE (MS micro+MS macro salts+MS vitamins, sucrose as a carbon source, myo-inositol, biotin, folic acid as additional non-MS vitamins, zeatin and thidiazuron as growth regulators of the cytokinin family of growth regulators (for further details of the medium composition see table A below)) is added on top of the solid medium. For 100 ml of solid medium 3 ml liquid KE will be used. The jars are placed in the dark at 22-24° C. for four weeks. After four weeks the same procedure, as described above, for proliferation can be repeated.

At each subculture the proliferation rate or multiplication rate can be determined by dividing the number of filaments formed (after separating or cutting the tissue back to the original number of nodes) by the initial number of filaments. The proliferation rates are determined for 10 genotypes for 3 subcultures (see table 5 below).

TABLE 5

| Proliferation rates of 10 genotypes | | | |
|---|---|---|---|
| subculture | 1 | 2 | 3 |
| Apache | 4.7 | 5.0 | 3.7 |
| Mirage | 5.2 | 5.0 | 4.7 |
| Charlotte | 4.7 | 5.1 | 4.2 |
| Helios | 5.2 | 5.2 | 3.7 |
| Olavi | 5.4 | 4.9 | 3.6 |
| Verseau | 4.3 | 4.0 | 4.4 |

TABLE 5-continued

Proliferation rates of 10 genotypes

| subculture | 1 | 2 | 3 |
|---|---|---|---|
| P. Blanche | 4.7 | 5.5 | 3.9 |
| Super Rose | 5.0 | 4.4 | 3.9 |
| Philiomel 1 | 4.8 | 4.8 | 4.5 |
| Balcon Rose | 4.5 | 5.0 | 3.6 |
| average | 4.9 | 4.9 | 4.0 |

3.3 Rooting

For rooting smaller explants are used. Each filament contains one or two axillary nodes. The explants are transferred to ventilated containers (ecoline boxes with XXL filter). The rooting medium is MS0-2 (half strength MS macro salts, full strength MS micro salts and MS vitamins, sucrose as the carbon source, myo-inositol, biotin, folic acid as additional non-MS vitamins, and plant agar as the solidifying agens) or RAI2-2 (half strength MS macro salts, full strength MS micro salts and MS vitamins, sucrose as the carbon source, myo-inositol, biotin, folic acid as additional non-MS vitamins, indole-acetic acid, indole-butyric acid as growth regulators of the auxin family of growth regulators, and plant agar as the solidifying agens).

Both media can be used and will give similar results. Plants are rooted for four weeks at a temperature of between 22° C. and 24° C. in a 16 h photoperiod of app. 3000 lux. Rooting percentages are determined for 10 genotypes, after 4 weeks (see table 6 below).

TABLE 6

Rooting % of 10 genotypes

| genotype | MS0-2 | RAI2-2 |
|---|---|---|
| Apache | 93 | 100 |
| Helios | 91 | 91 |
| Charlotte | 97 | 97 |
| Olavi | 90 | 85 |
| Mirage | 95 | nd |
| S. Rose | 87 | 100 |
| P. Blanche | 79 | 93 |
| Philiomel 1 | 100 | 100 |
| B. Rose | 88 | 83 |
| Verseau | 82 | 100 |
| average | 90 | 94 |

The rooted plantlets are taken out of the containers and washed in water to remove traces of medium and agar. The plantlets are transferred to soil in the greenhouse at 20° C. where they acclimatized and are treated as normal tissue culture plants.

TABLE A

| Compound | Media | | | | |
|---|---|---|---|---|---|
| | MS0 | MS0-2 | MS1 | MS1-2 | MS2Z |
| Macro Elements | MS | MS half | MS | MS half | MS |
| $KNO_3$ | 1.9 g·l$^{-1}$ | 0.95 g·l$^{-1}$ | 1.9 g·l$^{-1}$ | 0.95 g·l$^{-1}$ | 1.9 g·l$^{-1}$ |
| $NH_4NO_3$ | 1.65 g·l$^{-1}$ | 0.825 g·l$^{-1}$ | 1.65 g·l$^{-1}$ | 0.825 g·l$^{-1}$ | 1.65 g·l$^{-1}$ |
| $Ca(NO_3)_2$ x 4 $H_2O$ | — | — | — | — | — |
| $CaCl_2$ x 2 $H_2O$ | 0.44 g·l$^{-1}$ | 0.22 g·l$^{-1}$ | 0.44 g·l$^{-1}$ | 0.22 g·l$^{-1}$ | 0.44 g·l$^{-1}$ |
| $MgSO_4$ x 7 $H_2O$ | 0.37 g·l$^{-1}$ | 0.185 g·l$^{-1}$ | 0.37 g·l$^{-1}$ | 0.185 g·l$^{-1}$ | 0.37 g·l$^{-1}$ |
| $KH_2PO_4$ | 0.17 g·l$^{-1}$ | 0.085 g·l$^{-1}$ | 0.17 g·l$^{-1}$ | 0.085 g·l$^{-1}$ | 0.17 g·l$^{-1}$ |
| Micro-Elements | MS | MS | MS | MS | MS |
| vitamins | MS | MS | MS | MS | MS |
| sucrose | 30 g·l$^{-1}$ | 30 g·l$^{-1}$ | 30 g·l$^{-1}$ | 30 g·l$^{-1}$ | 30 g·l$^{-1}$ |
| myo-inositol | 0.1 g·l$^{-1}$ | 0.1 g·l$^{-1}$ | 0.1 g·l$^{-1}$ | 0.1 g·l$^{-1}$ | 0.1 g·l$^{-1}$ |
| biotin | 0.05 mg·l$^{-1}$ | 0.05 mg·l$^{-1}$ | 0.05 mg·l$^{-1}$ | 0.05 mg·l$^{-1}$ | 0.05 mg·l$^{-1}$ |
| folic acid | 0.5 mg·l$^{-1}$ | 0.5 mg·l$^{-1}$ | 0.5 mg·l$^{-1}$ | 0.5 mg·l$^{-1}$ | 0.5 mg·l$^{-1}$ |
| PVP (polyvinyl pyrrolidone) | | | 0.5 g·l$^{-1}$ | 0.5 g·l$^{-1}$ | |
| BA (6-benzylaminopurine) | | | 0.1 mg·l$^{-1}$ | 0.1 mg·l$^{-1}$ | |
| 2iP (2-isopentenyl-adenine) | | | 0.1 mg·l$^{-1}$ | 0.1 mg·l$^{-1}$ | |
| zeatine | | | | | 0.2 mg·l$^{-1}$ |
| thidiazuron (TDZ) | | | | | |
| IAA (Indole -3-Acetic Acid) | | | | | |
| IBA (Indole-Butyric Acid) | | | | | |
| plant agar | 6 g·l$^{-1}$ | 6 g·l$^{-1}$ | 6 g·l$^{-1}$ | 6 g·l$^{-1}$ | 6 g·l$^{-1}$ |
| pH | 5.8 (before autoclav) | 5.8 (before autoclav) | 5.8 (before autoclav) | 5.8 (before autoclav) | 5.8 (before autoclav) |

| Compound | SP1 | B1 | KE | RAI2-2 |
|---|---|---|---|---|
| Macro Elements | MS mod. | MS | MS | MS half |
| $KNO_3$ | 1.8 g·l$^{-1}$ | 1.9 g·l$^{-1}$ | 1.9 g·l$^{-1}$ | 0.95 g·l$^{-1}$ |
| $NH_4NO_3$ | 0.4 g·l$^{-1}$ | 1.65 g·l$^{-1}$ | 1.65 g·l$^{-1}$ | 0.825 g·l$^{-1}$ |
| $Ca(NO_3)_2$ x 4 $H_2O$ | 1.2 g·l$^{-1}$ | — | — | — |
| $CaCl_2$ x 2 $H_2O$ | | 0.44 g·l$^{-1}$ | 0.44 g·l$^{-1}$ | 0.22 g·l$^{-1}$ |
| $MgSO_4$ x 7 $H_2O$ | 0.36 g·l$^{-1}$ | 0.37 g·l$^{-1}$ | 0.37 g·l$^{-1}$ | 0.185 g·l$^{-1}$ |
| $KH_2PO_4$ | 0.27 g·l$^{-1}$ | 0.17 g·l$^{-1}$ | 0.17 g·l$^{-1}$ | 0.085 g·l$^{-1}$ |
| Micro-Elements | MS | MS | MS | MS |
| vitamins | MS | MS | MS | MS |
| sucrose | 20 g·l$^{-1}$ | 30 g·l$^{-1}$ | 30 g·l$^{-1}$ | 10 g·l$^{-1}$ |
| myo-inositol | 0.1 g·l$^{-1}$ | 0.1 g·l$^{-1}$ | 0.1 g·l$^{-1}$ | 0.1 g·l$^{-1}$ |
| biotin | 0.1 mg·l$^{-1}$ | 0.05 mg·l$^{-1}$ | 0.05 mg·l$^{-1}$ | 0.05 mg·l$^{-1}$ |

TABLE A-continued

| Media | | | | |
|---|---|---|---|---|
| folic acid | 0.5 mg·l$^{-1}$ | 0.5 mg·l$^{-1}$ | 0.5 mg·l$^{-1}$ | 0.5 mg·l$^{-1}$ |
| PVP (polyvinyl pyrrolidone) | — | | | |
| BA (6-benzylaminopurine) | 0.25 mg·l$^{-1}$ | 5.0 mg·l$^{-1}$ | | |
| 2iP (2-isopentenyl-adenine) | | | | |
| zeatine | | | 0.2 mg·l$^{-1}$ | 0.2 mg·l$^{-1}$ |
| thidiazuron (TDZ) | | | | 0.05 mg·l$^{-1}$ |
| IAA (Indole-3-Acetic Acid) | 0.1 mg·l$^{-1}$ | | | 0.5 mg·l$^{-1}$ |
| IBA (Indole-Butyric Acid) | | | | 0.5 mg·l$^{-1}$ |
| plant agar | 6 g·l$^{-1}$ | | | 6 g·l$^{-1}$ |
| pH | 5.8 (before autoclav) | 5.8 (before autoclav) | 5.8 (before autoclav) | 5.8 (before autoclav) |

The invention claimed is:

1. A method for the production of young plants selected from the group consisting of *Asteraceae* and *Violaceae*, which method comprises an in vitro culture phase during which explants obtained from a parent stock of a species to be propagated, or derivatives of these explants, are subjected to micropropagation which is carried out under suitable conditions and on suitable culture media, in order to produce micro-plantlets which, when subjected to an in vivo culture phase, are intended to develop into plants, characterized in that, to carry out said micropropagation:
   a) explants comprising stems or branches, each comprising meristems, are obtained from parent stock of species to be propagated, or from derivatives of these explants,
   b) the explants are, under axenic conditions and in the dark, placed on a shoot initiation medium which is composed such as to suit each plant species to be propagated, resulting in the induction of a first generation of white filaments which first generation of filaments comprise one or more axillary buds,
   c) each of the white filaments is divided into a plurality of pieces, each of which comprises an axillary bud, but at least one axillary bud, and said filaments and/or pieces obtained from a first generation of white filaments are returned under axenic conditions and in the dark to a proliferation medium for a period of time sufficient to allow the tissue of the plant cuttings to multiply, and to produce a large quantity of etiolated white filaments comprising between 2 and 10 axillary nodes, so as to induce the formation of a new generation of white filaments, and the procedure is repeated as often as necessary to produce different consecutive generations of white filaments until the desired amount of white filaments has been obtained,
   d) and said filaments and/or pieces are, in the light, under axenic conditions, placed on or into a rooting medium, which allows each axillary bud to produce a micro-plantlet which has roots, wherein the white filaments are, at ambient temperature, and in the dark, stored in a proliferation medium which is periodically changed, before being subjected to the rooting phase, during which each bud produces a rooted micro-plantlet intended to provide a young plant.

2. The method according to claim 1, characterized in that the meristems taken from parent stock are used as explants which are grown under axenic conditions in the light for a first period of time on a development medium common to each plant variety to be propagated, in order to bring about the formation of little plantlets which have first leaf primordia and then, for a second period of time, on a rooting medium common to each plant variety, in order to obtain rooted plantlets which are free from bacteria and viruses and which are intended to be placed on the proliferation medium in the dark in order to produce said white filaments.

3. The method according to claim 1, characterized in that the explants are taken from certified, bacteria- and virus-free parent stock.

4. The method according to claim 1, characterized in that the filaments and/or pieces thereof obtained from a first generation of white filaments are returned under axenic conditions to a fresh proliferation medium and grown in the dark for a period of time so as to induce the formation of a new generation of white filaments, and that the procedure is repeated as often as necessary to produce different consecutive generations of white filaments until the desired amount of white filaments has been obtained.

5. The method according to claim 1, characterized in that a two-layer cultivation system is employed in order to promote shoot multiplication characterized in that the shoot initiation and/or the proliferation medium is provided in the form of a two layer system comprising a solidified bottom layer comprising essentially macro- and micro-elements, vitamins and a carbon source, but no growth regulator, which bottom layer is overlayed with a fluid top layer comprising a growth regulator, which supports shoot multiplication by promoting the breakage and development of axillary buds into etiolated shoots and further into white filaments and/or the growth of the developing shoots into shoots comprising between 2 and 10 axillary nodes.

6. The method according to claim 1, characterized in that a culture medium of the "MS" type is used as the shoot initiation and/or proliferation medium, supplemented with a growth regulator being provided in a concentration which supports shoot multiplication by promoting the breakage and development of axillary buds into etiolated shoots and further into white filaments and/or the growth of the developing shoots into shoots comprising between 2 and 10 axillary nodes.

7. The method according to claim 1, characterized in that the shoot initiation and/or proliferation medium comprises a growth regulator belonging to the cytokinin family of growth regulators or a combination of growth regulators belonging to the cytokinin family of growth regulators and to the auxin family of growth regulators.

8. The method according to claim 7, characterized in that the growth regulators belonging to the cytokinin family of growth regulators or to the auxin family of growth regulators are provided in a concentration of between 0.01 mg/l and 5.0 mg/l.

9. The method according to claim 1, characterized in that the white filaments are stored at a temperature of between 2° C. and 10° C. for up to 10 months before being subjected to the rooting phase.

* * * * *